United States Patent
Dubois

(10) Patent No.: US 8,324,432 B2
(45) Date of Patent: Dec. 4, 2012

(54) METHOD FOR PRODUCING ACROLEIN BY MEANS OF DEHYDRATION OF GLYCEROL

(75) Inventor: Jean-Luc Dubois, Millery (FR)

(73) Assignee: Arkema France, Colombes Cedex (FR)

( * ) Notice: Subject to any disclaimer, the term of this patent is extended or adjusted under 35 U.S.C. 154(b) by 186 days.

(21) Appl. No.: 12/995,787

(22) PCT Filed: May 29, 2009

(86) PCT No.: PCT/FR2009/051019
§ 371 (c)(1),
(2), (4) Date: Dec. 2, 2010

(87) PCT Pub. No.: WO2009/156664
PCT Pub. Date: Dec. 30, 2009

(65) Prior Publication Data
US 2011/0082319 A1    Apr. 7, 2011

(30) Foreign Application Priority Data
Jun. 3, 2008   (FR) ..................... 08 53668

(51) Int. Cl.
*C07C 45/52* (2006.01)
(52) U.S. Cl. ....................... 568/449; 568/485

(58) Field of Classification Search .......... 568/449, 568/485
See application file for complete search history.

(56) References Cited

FOREIGN PATENT DOCUMENTS
WO    2006087083 A2    8/2006

OTHER PUBLICATIONS
World IP Organization. "International Search Report." PCT/FR2009/051019, Applicant: Arkema France, Mailed: Jan. 12, 2010.

*Primary Examiner* — Sikarl Witherspoon
(74) *Attorney, Agent, or Firm* — Millen, White, Zelano & Branigan, P.C.

(57) ABSTRACT

The invention relates to a method for the synthesis of acrolein by means of dehydration of the glycerol in the presence of a solid acid catalyst having a Hammett acidity of less than +2, such as sulfated zirconium oxides, phosphated zirconium oxides, tungstated zirconium oxides, silicated zirconium oxides, sulfated tin or titanium oxides, phosphated aluminas or silicas, doped iron phosphates, and phosphotungstic or silicotungstic acid salts placed in a reactive medium comprising a gaseous phase containing between 1 and 3000 ppm of an acid compound according to the Pearson classification, selected, for example, from SO3, SO2, and NO2, the dehydration reaction being carried out either in a gaseous phase or in a liquid phase.

15 Claims, No Drawings

METHOD FOR PRODUCING ACROLEIN BY MEANS OF DEHYDRATION OF GLYCEROL

The present invention relates to an improved process for the manufacture of acrolein by dehydration of glycerol in the presence of acid gas additives.

Acrolein is the simplest of the unsaturated aldehydes. It is also known as 2-propenal, acrylaldehyde or acrylic aldehyde. Due to its structure, acrolein has a high reactive power by virtue of the presence of its two reactive functional groups, which are capable of reacting individually or together. This is why acrolein has numerous applications, in particular as synthetic intermediate. It is in particular a key intermediate in the synthesis of methionine, a synthetic amino acid used as animal food supplement which is becoming established as a replacement for fish meal. Acrolein is a nonisolated intermediate in the synthesis of acrylic acid in the industrial production of acrylic acid by catalytic oxidation of propylene in the gas phase. The importance of the chemistry of acrylic acid and of its derivatives is known. Acrolein also results, by reaction with methyl vinyl ether followed by hydrolysis, in glutaraldehyde, which has numerous uses in the tanning of leather, as biocide in oil drilling operations and during the treatment of cutting oils, and as chemical disinfectant and sterilizing agent for hospital equipment.

The most commonly used process for the production of acrolein is based on the gas-phase catalytic oxidation reaction of propylene with atmospheric oxygen.

The acrolein thus obtained can then be directly incorporated in a process for the manufacture of acrylic acid. When the acrolein is used as starting material for the synthesis of methionine and/or acrylic acid and/or acrylonitrile or for fine chemistry reactions, a purification section makes it possible to remove the reaction byproducts, mainly carbon oxides, acrylic acid, acetic acid and acetaldehyde.

The production of acrolein is thus highly dependent on the propylene starting material obtained by steam cracking or catalytic cracking of petroleum fractions. This starting material, of fossil origin, furthermore contributes to increasing the greenhouse effect. It thus appears necessary to have available a process for the synthesis of acrolein which is not dependent on the propylene resource and which uses another starting material, preferably a renewable starting material. This process would be particularly advantageous for the synthesis of methionine and other products, which could then be said to be "obtained from biomass". This is because methionine, when used in animal food, is rapidly metabolized and the carbon dioxide gas which ends up in the atmosphere contributes to increasing the greenhouse effect. If the acrolein is obtained from a renewable starting material, for example obtained from vegetable oil, the $CO_2$ emissions no longer come within the balance of the process as they compensate for the carbon dioxide gas used by the biomass for its growth; there is therefore no increase in the greenhouse effect. Such a process then meets the criteria associated with the new concept of "green chemistry" in a broader context of sustainable development.

It is also known to synthesize aldehydes, such as acrolein, by dehydration of a polyalcohol, such as glycerol. Glycerol (also known as glycerin when it is in the form of an aqueous solution) results in particular from the methanolysis of vegetable and animal oils at the same time as the methyl esters, which are for their part employed in particular as fuels in diesel oil and heating oil. This is a natural product, available in large amounts; it can be stored and transported without difficulty. It exhibits the advantage of being a renewable starting material meeting the criteria associated with the new concept of "green chemistry".

Numerous recent studies have been devoted to the recovery in value of glycerol and in particular to the preparation of acrolein. The process which is the subject of these studies employs a reaction for the dehydration of glycerol according to the consecutive reactions:

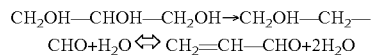

which make it possible to obtain acrolein.

This reaction is an equilibrium reaction; as a general rule, the hydration reaction is favored at low temperatures and the dehydration is favored at high temperatures. In order to obtain the acrolein, it is thus necessary to employ a sufficient temperature and/or a partial vacuum in order to displace the reaction. The reaction can be carried out in the liquid phase or in the gas phase. This type of reaction is known to be catalyzed by acids.

According to patent FR 69.5931, acrolein is obtained by passing glycerin vapors at a sufficiently high temperature over salts of acids having at least three acid functional groups, such as, for example, salts of phosphoric acid. The yields shown are greater than 75% after fractional distillation.

In U.S. Pat. No. 2,558,520, the dehydration reaction is carried out in the gas/liquid phase in the presence of diatomaceous earths impregnated with phosphoric acid salts, in suspension in an aromatic solvent. A degree of conversion of the glycerol to give acrolein of 72.3% is obtained under these conditions.

The process described in application WO 99/05085 is based on complex homogeneous catalysis under a $CO/H_2$ atmosphere under a pressure of 20/40 bar and in the presence of a solvent, such as an aqueous sulfolane solution.

Chinese patent application CN 1394839 relates to a process for the preparation of 3-hydroxypropanaldehyde from glycerol. Acrolein, an intermediate reaction product, is obtained by passing pure vaporized glycerol over a catalyst of potassium sulfate or magnesium sulfate type, and then the acrolein obtained is rehydrated to give hydroxypropanaldehyde. The reaction yields are not given.

U.S. Pat. No. 5,387,720 describes a process for the production of acrolein by dehydration of glycerol, in the liquid phase or in the gas phase, over solid acid catalysts defined by their Hammett acidity. The catalysts must have a Hammett acidity of less than +2 and preferably of less than −3. These catalysts correspond, for example, to natural or synthetic siliceous materials, such as mordenite, montmorillonite or acid zeolites; supports, such as oxides or siliceous materials, for example alumina ($Al_2O_3$) or titanium oxide ($TiO_2$), covered with mono-, di- or triacidic inorganic acids; oxides or mixed oxides, such as γ-alumina or $ZnO$—$Al_2O_3$ mixed oxide, or heteropolyacids. According to that patent, use is made of an aqueous solution comprising from 10 to 40% of glycerol and the operation is carried out at temperatures of between 180 and 340° C. in the liquid phase and between 250 and 340° C. in the gas phase. According to the authors of that patent, the gas-phase reaction is preferable as it makes it possible to have a degree of conversion of the glycerol of approximately 100%, which results in an aqueous acrolein solution containing byproducts. A proportion of approximately 10% of the glycerol is converted to hydroxypropanone, which occurs as predominant byproduct it the acrolein solution. The acrolein is recovered and purified by fractional condensation or distillation. For a liquid-phase reaction, a conversion limited to 15-25% is desired, in order to avoid an excessively great loss in selectivity. U.S. Pat. No. 5,426,249 describes the same gas-phase process for the dehydration of glycerol to give acrolein but followed by hydration of the acrolein and by hydrogenation to result in 1,2- and 1,3-propanediol.

The reaction for the dehydration of glycerol to give acrolein is thus generally accompanied by side reactions resulting in the formation of byproducts, such as hydroxypropanone, propanal, acetaldehyde, acetone, addition products of the acrolein with glycerol (known as acetals), polycondensation products of glycerol, cyclic glycerol ethers, and the like, but also of phenol and polyaromatic compounds, which are the cause of the formation of coke on the catalyst. This results, on the one hand, in a reduction in the yield and in the selectivity for acrolein and, on the other hand, in a deactivation of the catalyst. The presence of the byproducts in the acrolein, such as hydroxypropanone or propanal, some being furthermore difficult to isolate, requires separation and purification stages which result in high costs for the recovery of the purified acrolein. Furthermore, it is necessary to regenerate the catalyst very often, so as to regain a satisfactory catalytic activity.

The Applicant Company has attempted to solve these problems by proposing, in the French patent published under No. 2 882 052, to carry out the reaction for the dehydration of glycerol in the presence of molecular oxygen. It was observed on this occasion that, surprisingly, the introduction of oxygen reduces the formation of aromatic compounds, such as phenol, and of byproducts resulting from a hydrogenation of dehydrated products, such as propanal and acetone, but also of hydroxypropanone. The formation of coke on the catalyst is found to be reduced. This results in inhibition of the deactivation of the catalyst and in continuous regeneration of the catalyst. Some byproducts are found to be present in markedly lower amounts, which facilitates the subsequent purification stages.

Advantageous as they may be, these results are not sufficient economically to move to an industrial scale. Furthermore, the implementation of the process in the presence of oxygen involves operational precautions in order to prevent it from running away by proceeding as far as combustion, with its risks of explosion. This results, for example, in the use of an inert gas in order to remain outside the flammability zone. The nitrogen in the air can constitute a portion of this inert gas but will often be in an insufficient amount which will result in the use of additional inert gases, such as recycle gases comprising, in addition to nitrogen, which has not been able to react, the combustion gases and rare gases, such as argon, but also gases deliberately added, such as the above-mentioned gases but also methane and light alkanes. The use of inert gases, which, by definition, do not contribute to the reaction, involves the use of a large reactor, in comparison with what is necessary for the reactants alone. This results in an additional expenditure. This is the reason why the Applicant Company has continued its studies in order to improve the selectivity for acrolein of the reaction by focusing on the conditions of effectiveness and/or of selectivity of the catalysts already known for being used for the synthesis of acrolein from glycerol.

The Applicant Company has discovered with surprise that the catalysts of acid type known for the catalysis of the dehydration reaction which are solid homogeneous or multiphase materials insoluble in the reaction medium which, although acids, can also exhibit some undesirable sites probably the cause of the formation of the byproducts by reaction mechanisms which are sometimes not easy to predict.

The aim of the present invention is to overcome these disadvantages by implementing the process while adding, to the gaseous reaction medium, a compound capable of being attached, at least temporarily, to these sites and by inhibiting them during the process to prevent the formation of the byproducts.

A subject matter of the present invention is a process for the synthesis of acrolein by dehydration of glycerol in the presence of a solid acid catalyst, characterized in that it is implemented in a reaction medium comprising a gas phase comprising an acid compound.

The term "acid compound" is understood to mean, within the meaning of the present invention, a compound which, in addition to that which will be specified below, will exhibit, in solution with water, a pKa of less than 6.3. In particular, $CO_2$ is not an acid within the meaning of the present invention.

The dehydration reaction is carried out, for example, over solid acid catalysts, such as those described in French patent FR 2 882 052.

The catalysts which are suitable are homogeneous or multiphase materials which are insoluble in the reaction medium and which have a Hammett acidity, denoted $H_0$, of less than +2. As indicated in the U.S. Pat. No. 5,387,720, which makes reference to the paper by K. Tanabe et al. in "Studies in Surface Science and Catalysis", Vol. 51, 1989, Chap. 1 and 2, the Hammett acidity is determined by amine titration using indicators or by adsorption of a base in the gas phase. The catalysts meeting the criterion of acidity $H_0$ less than +2 can be chosen from natural or synthetic siliceous materials or acid zeolites; inorganic supports, such as oxides, covered with inorganic acids which are mono-, di- tri- or polyacids; oxides or mixed oxides, iron phosphates or heteropolyacids.

Advantageously, the catalysts are chosen from zeolites, Nafion® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$. According to the literature data, these catalysts all have a Hammett acidity $H_0$ of less than +2.

The preferred catalysts are sulfated zirconias, phosphated zirconias, tungstated zirconias, silica zirconias, sulfated titanium or tin oxides, phosphated aluminas or silicas, doped iron phosphates, or phosphor- or silicotungstic acid salts.

These catalysts all have a Hammett acidity $H_0$ of less than +2; the acidity $H_0$ can then vary to a large extent, down to values which can reach −20 in the reference scale with Hammett indicators. The table given on page 71 of the publication on acid/base catalysis (C. Marcilly), Vol. 1, in Editions Technip (ISBN No. 2-7108-0841-2), illustrates examples of solid catalysts within this acidity range.

The catalysts selected for this reaction are acid solids. The acidity of the solids can be measured in numerous ways and the Hammett method is only one of them.

The work by C. Marcilly referred to above furthermore lists various methods for measuring the acidity and the basicity of the solids.

Reference will be made to the publications by Aline Auroux, where various methods for measuring the acidity scales of solids are described, such as: A. Auroux and A. Gervasini, "J. Microcalorimetric Study of the Acidity and Basicity of Metal Oxide Surfaces", Phys. Chem., (1990) 94, 6371-79, and L. Damjanovic and A. Auroux, in "Handbook of Thermal Analysis and Calorimetry", Vol. 5, Chapter 11, pages 387-

485: Recent Advances, Techniques and Applications, M. E. Brown and P. K. Gallager, editors (2008 Elsevier B.V.).

Methods used to measure this acidity are described in patents EP 1 714 696 [0038 and 0039] and EP 1 714 955 [0045 and 0046] where the cases where the solid is white or not in color are distinguished.

These studies illustrate in particular that a solid is rarely composed either of solely acidic sites or of solely basic sites. Acid solids have most of the time both acidic sites, which are predominant, but also some basic sites. This dichotomy is illustrated in particular in the paper by A. Auroux and A. Gervasini oft page 6377, where FIG. 13 shows that one and the same oxide can simultaneously adsorb an acid compound, such as $CO_2$, and a basic compound, such as $NH_3$. Without wishing to be committed to any one theory, it is believed that the latter compounds contribute to the formation of the byproducts in the process.

The process is implemented in the presence of an acid compound present in the gas phase of the reaction medium which exhibits an affinity with the undesirable basic sites constituting the catalyst. This compound will be chosen from hard and soft acids as defined in the "Pearson" classification illustrated in the following papers: R. G. Pearson, J. Am. Chem. Soc., 85, 3533 (1963); R. G. Pearson, Science, 151 (1966), 172; R. G. Pearson, Chemistry in Britain, March 1967, 103; R. G. Pearson, J. Chemical Education, Vol. 45, No. 9 (1968), 581, and Vol. 45, No. 10 (1968), 643; R. G. Parr and R. G. Pearson, J. Am. Chem. Soc., (1983), 105, 7512.

It should be emphasized that, in the work by C. Marcilly referred to above, the scale based on the Pearson theory is used on pages 34 et seq.

These compounds can be gases under standard conditions but they can be either liquids or even solids if they are capable of passing into the gas phase of the reaction medium under the operating conditions of the process.

Preferably, the dehydration is carried out in the presence of a gas phase comprising a minor fraction of at least one acid compound within the meaning of the Pearson classification.

This acid compound will be chosen in particular from $SO_3$, $SO_2$, $NO_2$, and the like. It would not be departing from the scope of the invention if use were made of a mixture of these compounds. According to the Pearson theory, hard acids prefer to combine with hard bases and soft acids with soft bases. Use may be made of a mixture of compounds combining different acidities in order to inhibit the different, basic sites present on the catalyst.

The content of acid compounds will depend on the nature of the catalyst chosen for the dehydration reaction. It will generally be between 1 and 3000 ppm of the gas phase or, expressed as percentage by volume, from 0.0001 to 0.3%.

If the reaction is carried out in the liquid phase, the acid compound can be in liquid form or even in solid form, provided that it is capable, under the reaction conditions, of passing into the liquid phase to achieve the above contents or, in the case of a solid compound, of dissolving and then of passing into the liquid phase, as was specified above.

It should be noted that patent EP 1 253 132 describes a process for the synthesis of acrylic acid by oxidation of alkanes or acrolein in the presence of a reducing compound composed of organic acids (formic or oxalic acid) or compounds comprising sulfur, such as $SO_2$ or $H_2S$, $SO_2$ being preferred. However, it may be emphasized that it is not the same reaction with a different catalyst and that the activity of said compound is to stabilize the catalyst and not to increase its selectivity. The reaction according to the invention can be carried out in the gas phase or in the liquid phase, preferably in the gas phase.

When the reaction is carried out in the gas phase, different processing technologies can be used, namely fixed bed process, fluidized bed process or circulating fluidized bed process. In the first 2 processes, in a fixed bed or in a fluidized bed, the regeneration of the catalyst can be separated from the reaction.

It can be carried out ex situ, for example by extraction of the catalyst and combustion under air or with a gas mixture comprising molecular oxygen. In this case, the temperature and the pressure at which the regeneration is carried out do not have to be the same as those at which the reaction is carried out. Preferably, the addition of the acid compounds within the meaning of Pearson is carried out in the reactor and not during the regeneration.

According to the process of the invention, it can be carried out continuously in situ, at the same time as the reaction, in view of the presence of a small amount of molecular oxygen or of a gas comprising molecular oxygen in the reactor. In this case, the regeneration is similar to an inhibition of the deactivation and takes place at the temperature and the pressure of the reaction. Due to these specific conditions where the regeneration takes place continuously, the injection of the gaseous acid compound happens to be simultaneous and preferably upstream of the catalytic bed, so that the acid compounds are perfectly mixed in the reaction mixture.

In the circulating fluidized bed process, the catalyst circulates in two vessels, a reactor and a regenerator. It is known that the dehydration reaction is endothermic; it is therefore necessary to provide energy to the first vessel, whereas the regeneration, consisting of the combustion of the coke, is exothermic; it is therefore necessary to remove the heat from the second vessel. In the case of the circulating fluidized bed, the two systems can cancel each other out: according to the process of the invention, the regeneration of the catalyst under a stream of oxygen by combustion results in a reheating of the catalyst and consequently provides the energy necessary for the dehydration reaction when the reheated catalyst returns to the reactor. The residence time in each vessel depends on the rate of deactivation of the catalyst and on the amount of coke formed on the catalyst. Specifically, a minimum amount of coke is desirable in order to be able to bring the solid back to the favorable temperature and a maximum amount of coke is necessary in order to prevent the solid from deteriorating by sintering during the combustion. The injection of the gaseous acid compound is preferably carried out in the reactor.

The dehydration reaction is carried out in the gas phase in the presence of a catalyst at a temperature ranging from 150° C. to 500° C., preferably of between 250° C. and 350° C., and a pressure of between 1 and 5 bar.

The reaction is carried out in the liquid phase in the presence of a catalyst at a temperature ranging from 150° C. to 500° C., preferably of between 250° C. and 350° C., and a pressure of greater than 5 bar and preferably of between 20 and 80 bar.

The following examples illustrate the process of the present invention.

During the dehydration of glycerol in the presence of a conventional acid catalyst, acrolein is obtained but also byproducts, such as hydroxypropanone, propanal, acetaldehyde, acetone, phenol, the addition products of acrolein with glycerol, the polycondensation products of glycerol, and cyclic, or noncyclic glycerol ethers.

These examples illustrate the effect of the presence of the acid compound on the selectivity of the reaction with regard to the various known byproducts and in particular hydroxypropanone, which is the most evident compound and is thus representative of the effectiveness of the process. They will also illustrate the effects of the presence of acid compounds on the deactivation of the catalyst.

EXAMPLE 1

The reaction can be carried out under the following conditions. Use is made of a Pyrex reactor containing a catalyst bed held by a sintered glass. First of all a catalyst, such as the tungstated zirconia dehydration catalyst from DaiIchi Kigenso KK, reference Z1044, having a weight of approximately 6.6 g and reduced to a particle size of 0.1-0.15 mm, diluted with 7 ml of silicon carbide with a fine particle size (0.125 mm), is charged. Subsequently, a series of beds of silicon carbide with different particle sizes: 2 ml of 0.125 mm, 7 ml of 0.5 mm and, finally, 1.19 mm up to the top of the reactor, is charged.

The reactor is subsequently placed in an oven connected to the test installation. The temperature of the catalyst is temperature regulated at 305° C., measured in the "dehydration layer".

The reactor is fed via the top with a helium-krypton/$SO_2$/water-glycerol gas mixture at a pressure of 1.3 bar absolute. The helium-krypton gas mixture contains, 4.92% of krypton, which acts as internal standard. The water-glycerol mixture contains 30% by weight of glycerol.

The composition of the injected mixture is as follows, expressed as molar percentage:
helium/krypton/$O_2$/$SO_2$/water/glycerol: 50/2.6/3.4/0.02/40.6/3.4.

The flow rate for introduction of the charging mixture is such that the hourly space velocity (HSV) will be 2000 h$^{-1}$.

The hourly space velocity is equal to the ratio of the total gas flow rate of the gas mixture, expressed in standard liters per hour, to the bulk catalyst volume, expressed in liters.

The effluents are trapped in water at the outlet of the reactor with a trap cooled to 0° C., making it possible to separate the liquid effluents from the noncondensable effluents. The acrolein and the hydroxy-propanone, as model compound for the byproducts other than acrylic acid, are quantitatively determined by chromatographic analysis.

The effluents are accumulated in the trap for a period of 60 minutes. The noncondensable gases are analyzed throughout the duration of the balance. The yield of acrolein produced is 70 mol %, of acrylic acid 2 mol % and of hydroxyacetone 0.5 mol %.

EXAMPLE 2

Comparative

Example 1 will be repeated but in the absence of $SO_2$.

The effluents are accumulated in the trap for a period of 60 minutes. The noncondensable gases are analyzed throughout the duration of the balance. The yield of acrolein produced is 68 mol %, of acrylic acid 2 mol % and of hydroxyacetone 2 mol %.

EXAMPLE 3

Use is made of the same Pyrex reactor as in example 1, It is charged with a tungstated zirconia dehydration catalyst from Daiichi Kigenso Kagaku Kogyo, reference Z1044 ring, ground and sieved to a particle size of 0.32 to 0.50 mm, with a volume of 7 ml and a weight of 9.18 g. The undiluted catalyst is placed between 2 layers of silicon carbide.

The reactor is placed in an oven which is regulated at a temperature of 275° C. The reactor is fed with a gas mixture at 275° C. of $N_2$/$O_2$/$SO_2$/water/glycerol at a pressure of 1.3 bar absolute. This gas mixture is obtained by injecting, into an electric evaporator, on the one hand, a stream of nitrogen and a stream of oxygen which are controlled in flow rate by mass flow regulators and, on the other hand, a liquid stream of a mixture of glycerol (Prolabo), demineralized water and sulfurous acid comprising 7.4% of $SO_2$ (Sigma-Aldrich), via a volumetric pump of HPLC type, the flow rate of which is controlled by a balance.

The composition of the injected mixture is as follows, expressed as molar percentages:
$N_2$/$O_2$/$SO_2$/water/glycerol: 15.4/3.9/0.005/74.5/6.2.

The flow rate for introduction of the charging mixture is such that the hourly space velocity (HSV) is 4200 h$^{-1}$.

After injecting the gas mixture over the catalyst for 3 hours, a material balance is carried out for 90 minutes in the same way as in example 1. The results are given in table 1.

EXAMPLE 4

The conditions of example 3 are repeated with a gas mixture with the molar composition:
$N_2$/$O_2$/$SO_2$/water/glycerol: 15.4/3.9/0.025/74.5/6.2.

A balance is carried out after injecting the mixture for 3 hours and for 24 hours.

The results are given in table 1.

EXAMPLE 5

Comparative

The conditions of example 3 are reproduced with a gas mixture with the molar composition:
$N_2$/$O_2$/$SO_2$/water/glycerol: 15.4/3.9/0/74.5/6.2.

A balance is carried out after 3 hours and 24 hours.
The results are given in table 1.

TABLE 1

| Example | 3 | 4 | | 5 (comparative) | |
|---|---|---|---|---|---|
| Injection time (h) | 3 | 3 | 24 | 3 | 24 |
| $SO_2$ (mol %) | 0.005 | 0.025 | 0.025 | 0 | 0 |
| Glycerol conversion (%) | 100 | 100 | 87 | 100 | 69 |
| Acrolein yield (%) | 73 | 73 | 60 | 72 | 49 |
| Hydroxypropanone yield (%) | 0.4 | 0.2 | 5.9 | 2.4 | 5.9 |

It is found that the addition of $SO_2$ not only brings about an improvement in the yield but also limits the deactivation of the catalyst.

What is claimed is:

1. A process for the synthesis of acrolein, comprising dehydrating glycerol in the presence of a solid acid catalyst in a reaction medium comprising a gas phase comprising an acid compound.

2. The process as claimed in claim 1, wherein the catalyst has a Hammett acidity of less than +2.

3. The process as claimed in claim 2, wherein the catalyst is selected from the group consisting of zeolites, composites based on sulfonic acid of fluoropolymers, chlorinated aluminas, phosphotungstic acids, phosphotungstic acid salts, silicotungstic acids, silicotungstic acid salts, and solids of the type comprising metal oxides impregnated with acid functional groups.

4. The process as claimed in claim 3, wherein the catalyst is a sulfated zirconia, phosphated zirconia, tungstated zirconia, silica zirconia, sulfated titanium or tin oxide, phosphate alumina or silica, doped iron phosphate, or a phosphor- or silicotungstic acid salt.

5. The process as claimed in claim 1, wherein the dehydration is carried out in the presence of a gas phase comprising a minor fraction of at least one acid compound within the meaning of the Pearson classification.

6. The process as claimed in claim 5, wherein the acid compound is $SO_3$, $SO_2$ or $NO_2$.

7. The process as claimed in claim 1, wherein the content of acid compound in the gas phase is between 1 and 3000 ppm.

8. The process as claimed in claim 1, wherein the dehydration reaction is carried out in the gas phase at a temperature of between 150° C. and 500° C., and under a pressure of between 1 and 5 bar.

9. The process as claimed in claim 1, wherein the reaction is carried out in the liquid phase at a temperature of between 150° C. and 500° C., and under a pressure of greater than 5 bar.

10. The process as claimed in claim 3, wherein the catalyst is selected from the group consisting of solids of the type comprising metal oxides impregnated with acid functional groups, which are selected from the group consisting of tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ and silicoaluminate $SiO_2/Al_2O_3$, which are impregnated with acid functional groups selected from the group consisting of borate $BO_3$, sulfate $SO_4$, tungstate $WO_3$, phosphate $PO_4$, silicate $SiO_2$ and molybdate $MoO_3$.

11. The process as claimed in claim 3, wherein the catalyst is selected from the group consisting of zeolites, chlorinated aluminas, phosphotungstic acids, phosphotungstic acid salts, silicotungstic acids, and silicotungstic acid salts.

12. The process as claimed in claim 8, wherein the dehydration reaction is carried out in the gas phase at a temperature of between 250° C. and 350° C.

13. The process as claimed in claim 9, wherein the reaction is carried out in the liquid phase at a temperature of between 250° C. and 350° C.

14. The process as claimed in claim 13, wherein the reaction is carried out in the liquid phase under a pressure of between 20 and 80 bar.

15. The process as claimed in claim 9, wherein the reaction is carried out in the liquid phase under a pressure of between 20 and 80 bar.

* * * * *